United States Patent
Kang et al.

(10) Patent No.: US 10,315,977 B1
(45) Date of Patent: Jun. 11, 2019

(54) METHOD OF PREPARING N-BUTYRIC ACID BY USING POLY-3-HYDROXYBUTYRATE

(71) Applicant: Dongguan University of Technology, Dongguan (CN)

(72) Inventors: Shimin Kang, Dongguan (CN); Hang Zhang, Dongguan (CN); Jietai Li, Dongguan (CN); Zhilin Li, Dongguan (CN); Yongjun Xu, Dongguan (CN); Chenghua Sun, Dongguan (CN); Nanlong Hong, Dongguan (CN)

(73) Assignee: DONGGUAN UNIVERSITY OF TECHNOLOGY, Dongguan, Guangdong (CN)

( * ) Notice: Subject to any disclaimer, the term of this patent is extended or adjusted under 35 U.S.C. 154(b) by 0 days.

(21) Appl. No.: 16/203,479

(22) Filed: Nov. 28, 2018

(30) Foreign Application Priority Data

Sep. 26, 2018 (CN) .......................... 2018 1 1124638

(51) Int. Cl.
| | | |
|---|---|---|
| *C07C 51/00* | (2006.01) | |
| *C07C 53/00* | (2006.01) | |
| *C07C 51/377* | (2006.01) | |
| *C08G 63/06* | (2006.01) | |
| *C07C 53/124* | (2006.01) | |

(52) U.S. Cl.
CPC ............ *C07C 51/377* (2013.01); *C08G 63/06* (2013.01); *C07C 53/124* (2013.01)

(58) Field of Classification Search
CPC ............................ C07C 51/377; C07C 53/124
See application file for complete search history.

(56) References Cited

U.S. PATENT DOCUMENTS

| 5,468,627 A | * | 11/1995 | Gatfield | .................... | C12P 7/40 |
| | | | | | 435/141 |
| 6,395,520 B1 | * | 5/2002 | Babel | ..................... | C08G 63/06 |
| | | | | | 435/135 |
| 2008/0009652 A1 | * | 1/2008 | Shan | ..................... | C07C 51/083 |
| | | | | | 562/606 |

OTHER PUBLICATIONS

Zigova et al. Butyric acid production by Clostridium butyricum with integrated extraction and pertraction. Process Biochemistry vol. 34, 835-843. (Year: 1999).*

* cited by examiner

*Primary Examiner* — Sikarl A Witherspoon
(74) *Attorney, Agent, or Firm* — Aeon Law, PLLC; Adam L. K. Philipp; Regina Song

(57) ABSTRACT

The present invention relates to a method of preparing n-butyric acid by using poly-3-hydroxybutyrate. The method comprises following steps: placing poly-3-hydroxybutyrate in a closure means, passing hydrogen into the closure means to eliminate air after making an initial hydrogen pressure be 2 to 6 MPa, carrying out an agitation at 190 to 240° C. for reaction for 6 to 36 hours to obtain n-butyric acid. The preparation method provided by the present invention does not require a catalyst or a reaction solvent, and converts poly-3-hydroxybutyrate into n-butyric acid by a one-step reaction under a hydrogen atmosphere. The conversion rate of poly-3-hydroxybutyrate is 100%, the yield of n-butyric acid reaches up to 97%, the purity of n-butyric acid in all obtained liquid products reaches up to 98%, and no additional subsequent separation process is needed to the target product n-butyric acid.

7 Claims, 1 Drawing Sheet

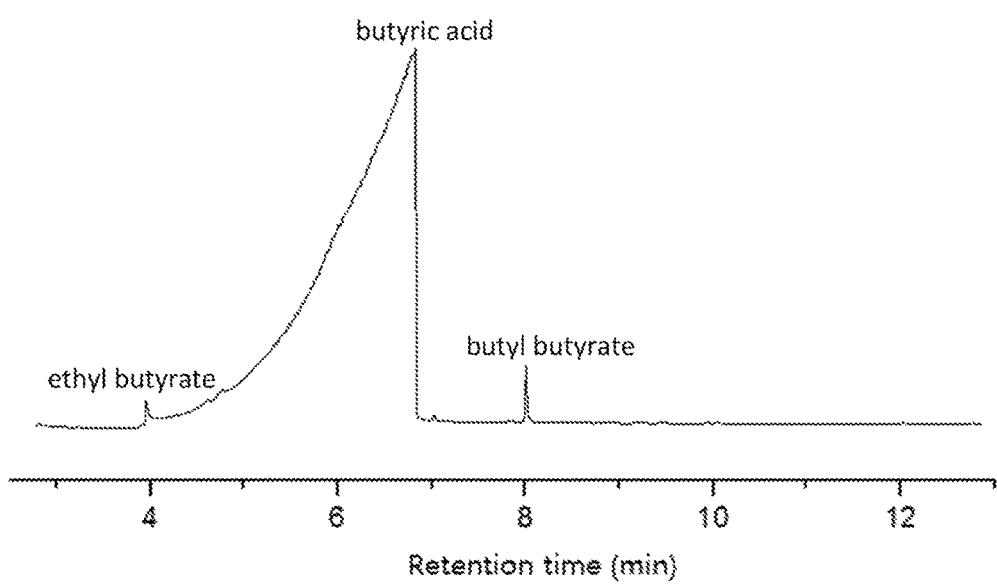

METHOD OF PREPARING N-BUTYRIC ACID BY USING POLY-3-HYDROXYBUTYRATE

TECHNICAL FIELD

The present invention pertains to the field of comprehensive utilization of poly-3-hydroxybutyrate, and in particular, relates to a method of preparing n-butyric acid by using poly-3-hydroxybutyrate.

BACKGROUND

Developing renewable biomass raw materials to replace increasingly depleted petrochemical resources for preparation of chemicals has attracted widespread attention. Poly-3-hydroxybutyrate is intracellular polyester synthesized by many kinds of microorganisms, and exists in microorganisms mainly as a storage material for carbon and energy sources. Poly-3-hydroxybutyrate can realize large-scale industrial production by microbial fermentation, and has become an important renewable biomass resource.

N-butyric acid is an important organic chemical, is for example widely used in perfume synthesis, and is used as a raw material for fine chemical products for synthesis of butyrate and cellulose butyrate. Current industrial production methods of n-butyric acid include fermentation and butyraldehyde oxidation. The fermentation method uses starch or sugar as a raw material to ferment with butyric acid bacteria to obtain n-butyric acid, but it also produces many by-products, and the target product n-butyric acid has low purity, resulting in high separation cost; meanwhile, the yield of n-butyric acid is not high, and a utilization rate of sugar raw material is low. The butyraldehyde oxidation method uses manganese acetate or cobalt acetate as a catalyst to oxidize butyraldehyde with air or oxygen, and after the oxidation reaction, butyric acid is obtained by fractionation. The problem of the butyraldehyde oxidation method is that it requires butyraldehyde which is relatively expensive as chemical raw material and metal manganese or cobalt which is harmful to the environment as catalyst.

Therefore, developing an environmentally friendly method using renewable biomass for preparing n-butyric acid with high yield and high purity has important research significance and application value.

SUMMARY OF THE INVENTION

An object of the present invention is to overcome defects and shortcomings of the prior art that production methods of n-butyric acid have high separation cost, low yield and environmental hazard, and to provide a method of preparing n-butyric acid by using poly-3-hydroxybutyrate. The preparation method provided by the present invention does not require a catalyst or a reaction solvent, and converts poly-3-hydroxybutyrate into n-butyric acid by a one-step reaction under a hydrogen atmosphere. The conversion rate of poly-3-hydroxybutyrate is 100%, the yield of n-butyric acid reaches up to 97%, the purity of n-butyric acid in all obtained liquid products reaches up to 98%, and no additional subsequent separation process is needed to obtain target product n-butyric acid.

In order to realize the above-described object, the present invention adopts the following technical solution:

a method of preparing n-butyric acid by using poly-3-hydroxybutyrate, comprising following steps: placing poly-3-hydroxybutyrate in a closure means, passing hydrogen into the closure means to eliminate air, after making an initial hydrogen pressure be 2 to 6 MPa, carrying out an agitation at 190 to 240° C. for reaction for 6 to 36 hours to obtain n-butyric acid.

The preparation method provided by the present invention does not require a catalyst or a reaction solvent, and converts poly-3-hydroxybutyrate into n-butyric acid by a one-step reaction under a hydrogen atmosphere (during the reaction, poly-3-hydroxybutyrate is first pyrolyzed into an unsaturated crotonic acid in the hydrogen atmosphere, and then unsaturated crotonic acid converts into n-butyric acid by hydrogenation reaction). The conversion rate of poly-3-hydroxybutyrate is 100%, the yield of n-butyric acid reaches up to 97%, the purity of n-butyric acid in all obtained liquid products reaches up to 98%, and no additional subsequent separation process is needed to obtain the target product n-butyric acid.

The present invention can further improve the yield of n-butyric acid by optimizing pressure of the atmosphere, reaction temperature and time.

Preferably, a temperature for the reaction is 200 to 220° C.

Preferably, a time for the reaction is 12 to 24 hours.
Preferably, the initial hydrogen pressure is 3 to 4 MPa.
Preferably, the agitation is a mechanical agitation.
Preferably, a rate of the agitation is 500 to 1000 r/min.
Conventional closure means in the art can be used in the present invention.

Preferably, the closure means is an autoclave.
Compared with the prior art, the present invention has following beneficial effects:

the preparation method provided by the present invention does not require catalyst or reaction solvent, and converts poly-3-hydroxybutyrate into n-butyric acid by a one-step reaction under a hydrogen atmosphere. The conversion rate of poly-3-hydroxybutyrate is 100%, the yield of n-butyric acid reaches up to 97%, the purity of n-butyric acid in all obtained liquid products reaches up to 98%, and no additional subsequent separation process is needed to obtain the target product n-butyric acid.

BRIEF DESCRIPTION OF THE DRAWINGS

FIG. 1 is a gas chromatography-mass spectrometry spectrum of a product after poly-3-hydroxybutyrate is reacted in Embodiment 1.

DETAILED DESCRIPTION OF THE PREFERED EMBODIMENT

The present invention is further described below in combination with embodiments. These embodiments are only intended to illustrate the present invention and are not intended to limit the scope of the present invention. Experimental methods in following embodiments, which do not specify specific conditions, are generally in accordance with conventional conditions in the art or in accordance with conditions recommended by the manufacturer. Raw materials, reagents, etc. used, unless otherwise specified, are raw materials and reagents available from commercial markets such as conventional market. Any non-substantial changes and substitutions made by those skilled in the art based on the present invention are within the scope of protection of the present invention.

Embodiment 1

A method of preparing n-butyric acid by poly-3-hydroxybutyrate, which is as follows:

5 g of poly-3-hydroxybutyrate was placed in a 300 mL high temperature high pressure autoclave, hydrogen was passed into the autoclave to eliminate air from the autoclave until the hydrogen pressure was maintained at 4 MPa, and then the autoclave was sealed. A mechanical agitation started, the rate of the mechanical agitation was controlled at 1000 r/min, the autoclave was warmed up to 200° C. at a rate of 4° C./min, and the reaction was carried out at the temperature of 200° C. for 24 hours. After the reaction, the temperature was cooled to room temperature, poly-3-hydroxybutyrate was completely converted, and liquid products with n-butyric acid as a main component were obtained (see FIG. 1). By gas chromatography quantitative analysis, the yield of n-butyric acid was determined to be 97%, and the purity of n-butyric acid in the liquid product was 98%.

Embodiment 2

A method of preparing n-butyric acid by poly-3-hydroxybutyrate, which is as follows:

5 g of poly-3-hydroxybutyrate was placed in a 300 mL high temperature high pressure autoclave, hydrogen was passed into the autoclave to eliminate air from the autoclave until the hydrogen pressure was maintained at 5 MPa, and then the autoclave was sealed. A mechanical agitation started, the rate of the mechanical agitation was controlled at 800 r/min, the autoclave was warmed up to 210° C. at a rate of 4° C./min, and the reaction was carried out at the temperature of 210° C. for 18 hours. After the reaction, the temperature was cooled to room temperature, poly-3-hydroxybutyrate was completely converted, and liquid products with n-butyric acid as a main component were obtained. By gas chromatography quantitative analysis, the yield of n-butyric acid was determined to be 95%, and the purity of n-butyric acid in the liquid product was 97%.

Embodiment 3

A method of preparing n-butyric acid by poly-3-hydroxybutyrate, which is as follows:

5 g of poly-3-hydroxybutyrate was placed in a 300 mL high temperature high pressure autoclave, hydrogen was passed into the autoclave to eliminate air from the autoclave until the hydrogen pressure was maintained at 3 MPa, and then the autoclave was sealed. A mechanical agitation started, the rate of the mechanical agitation was controlled at 800 r/min, the autoclave was warmed up to 220° C. at a rate of 4° C./min, and the reaction was carried out at the temperature of 220° C. for 12 hours. After the reaction, the temperature was cooled to room temperature, and liquid products with n-butyric acid as a main component were obtained.

Embodiment 4

A method of preparing n-butyric acid by poly-3-hydroxybutyrate, which is as follows:

5 g of poly-3-hydroxybutyrate was placed in a 300 mL high temperature high pressure autoclave, hydrogen was passed into the autoclave to eliminate air from the autoclave until the hydrogen pressure was maintained at 3 MPa, and then the autoclave was sealed. A mechanical agitation started, the rate of the mechanical agitation was controlled at 500 r/min, the autoclave was warmed up to 190° C. at a rate of 4° C./min, and the reaction was carried out at the temperature of 190° C. for 36 hours. After the reaction, the temperature was cooled to room temperature, and liquid products with n-butyric acid as a main component were obtained.

Embodiment 5

A method of preparing n-butyric acid by poly-3-hydroxybutyrate, which is as follows:

5 g of poly-3-hydroxybutyrate was placed in a 300 mL high temperature high pressure autoclave, hydrogen was passed into the autoclave to eliminate air from the autoclave until the hydrogen pressure was maintained at 5 MPa, and then the autoclave was sealed. A mechanical agitation started, the rate of the mechanical agitation was controlled at 500 r/min, the autoclave was warmed up to 240° C. at a rate of 4° C./min, and the reaction was carried out at the temperature of 240° C. for 6 hours. After the reaction, the temperature was cooled to room temperature, and liquid products with n-butyric acid as a main component were obtained.

Embodiment 6

A method of preparing n-butyric acid by poly-3-hydroxybutyrate, which is as follows:

5 g of poly-3-hydroxybutyrate was placed in a 300 mL high temperature high pressure autoclave, hydrogen was passed into the autoclave to eliminate air from the autoclave until the hydrogen pressure was maintained at 2 MPa, and then the autoclave was sealed. A mechanical agitation started, the rate of the mechanical agitation was controlled at 800 r/min, the autoclave was warmed up to 240° C. at a rate of 4° C./min, and the reaction was carried out at the temperature of 240° C. for 12 hours. After the reaction, the temperature was cooled to room temperature, and liquid products with n-butyric acid as a main component were obtained.

Those of ordinary skill in the art will appreciate that the embodiments herein are intended to assist the reader in understanding principles of the present invention, and it should be understood that the scope of protection of the present invention is not limited to such particular statements and embodiments. Those of ordinary skill in the art can make various other specific modifications and combinations without departing from the spirit of the present invention based on these technical teachings disclosed by the present invention, and these modifications and combinations are still within the scope of protection of the present invention.

What is claimed:

1. A method of preparing n-butyric acid by using poly-3-hydroxybutyrate, characterized in that, the method comprises following steps: placing poly-3-hydroxybutyrate in a closure means, passing hydrogen into the closure means to eliminate air after making an initial hydrogen pressure be 2 to 6 MPa, carrying out an agitation at 190 to 240° C. for reaction for 6 to 36 hours to obtain n-butyric acid.

2. The method of preparing n-butyric acid by using poly-3-hydroxybutyrate according to claim 1, wherein a temperature for the reaction is 200 to 220° C.

3. The method of preparing n-butyric acid by using poly-3-hydroxybutyrate according to claim 1, wherein a time for the reaction is 12 to 24 hours.

4. The method of preparing n-butyric acid by using poly-3-hydroxybutyrate according to claim 1, wherein the initial hydrogen pressure is 3 to 4 MPa.

5. The method of preparing n-butyric acid by using poly-3-hydroxybutyrate according to claim 1, wherein the agitation is a mechanical agitation.

6. The method of preparing n-butyric acid by using poly-3-hydroxybutyrate according to claim 1, wherein a rate of the agitation is 500 to 1000 r/min.

7. The method of preparing n-butyric acid by using poly-3-hydroxybutyrate according to claim 1, wherein the closure means is an autoclave.

* * * * *